US009072481B2

(12) United States Patent
Shelhamer

(10) Patent No.: US 9,072,481 B2
(45) Date of Patent: Jul. 7, 2015

(54) APPARATUS AND METHOD FOR ASSESSING VESTIBULO-OCULAR FUNCTION

(75) Inventor: Mark J. Shelhamer, Reistertown, MD (US)

(73) Assignee: The Johns Hopkins University, Baltimore, MD (US)

( * ) Notice: Subject to any disclaimer, the term of this patent is extended or adjusted under 35 U.S.C. 154(b) by 523 days.

(21) Appl. No.: 13/229,403

(22) Filed: Sep. 9, 2011

(65) Prior Publication Data

US 2012/0065549 A1 Mar. 15, 2012

Related U.S. Application Data

(60) Provisional application No. 61/381,177, filed on Sep. 9, 2010.

(51) Int. Cl.
*A61B 5/00* (2006.01)
*A61B 5/11* (2006.01)

(52) U.S. Cl.
CPC .............. *A61B 5/4023* (2013.01); *A61B 5/11* (2013.01); *A61B 5/6803* (2013.01); *A61B 5/742* (2013.01); *A61B 5/6814* (2013.01)

(58) Field of Classification Search
CPC .............. G02B 2027/0187; A61B 2562/0219; A61B 3/113; A61B 5/11; A61B 5/6803

USPC .......................................... 600/558, 587, 595
See application file for complete search history.

(56) References Cited

U.S. PATENT DOCUMENTS

| 5,360,971 | A * | 11/1994 | Kaufman et al. | 250/221 |
|---|---|---|---|---|
| 5,517,021 | A * | 5/1996 | Kaufman et al. | 250/221 |
| 7,789,838 | B2 * | 9/2010 | Merfeld et al. | 600/559 |
| 8,529,463 | B2 * | 9/2013 | Della Santina et al. | 600/558 |
| 2004/0122790 | A1* | 6/2004 | Walker et al. | 707/1 |
| 2006/0005846 | A1* | 1/2006 | Krueger et al. | 128/898 |
| 2006/0209013 | A1* | 9/2006 | Fengels | 345/156 |
| 2008/0015462 | A1* | 1/2008 | Merfeld et al. | 600/559 |
| 2010/0198104 | A1* | 8/2010 | Schubert et al. | 600/558 |
| 2011/0152711 | A1* | 6/2011 | Della Santina et al. | 600/546 |

* cited by examiner

*Primary Examiner* — Sean Dougherty
(74) *Attorney, Agent, or Firm* — Venable LLP; Henry J. Daley; Todd R. Farnsworth

(57) ABSTRACT

A system for assessing vestibulo-ocular function includes a motion sensor system adapted to be coupled to a user's head; a data processing system configured to communicate with the motion sensor system to receive the head-motion signals; a visual display system configured to communicate with the data processing system to receive image signals from the data processing system; and a gain control device arranged to be operated by the user and to communicate gain adjustment signals to the data processing system.

9 Claims, 5 Drawing Sheets

US 9,072,481 B2

APPARATUS AND METHOD FOR ASSESSING VESTIBULO-OCULAR FUNCTION

CROSS-REFERENCE OF RELATED APPLICATION

This application claims priority to U.S. Provisional Application No. 61/381,177 filed Sep. 9, 2010, the entire contents of which are hereby incorporated by reference.

This invention was made with Government support of Grant No. T32 EB003383, awarded by the Department of Health and Human Services, The National Institutes of Health (NIH); and Grant No. NNX10AO19G, awarded by NASA. The U.S. Government has certain rights in this invention.

BACKGROUND

1. Field of Invention

The field of the currently claimed embodiments of this invention relates to systems and methods for assessing vestibulo-ocular function, and more particularly to systems and methods for assessing vestibulo-ocular function without measuring eye movements.

2. Discussion of Related Art

Assessment of vestibular function is crucial in a great many experimental and clinical settings. One of the most fundamental vestibular functions is control of eye motion during head motion so that stable vision is maintained. If the vestibulo-ocular reflex (VOR) is miscalibrated (i.e., the eye movements do not appropriately compensate for head movements), a stationary target will appear to move when the head moves (oscillopsia). The accuracy of this VOR is typically measured by recording eye movements during controlled head movements. However, eye-movement measurement can be time-consuming, expensive, and invasive, often requiring specialized training for proper configuration and operation of delicate equipment. Consequently, there remains a need for improved systems and methods for assessing vestibulo-ocular function.

SUMMARY

A system for assessing vestibulo-ocular function according to an embodiment of the current invention includes a motion sensor system adapted to be coupled to a user's head, wherein the motion sensor system provides head-motion signals based on motion of the user's head; a data processing system configured to communicate with the motion sensor system to receive the head-motion signals; a visual display system configured to communicate with the data processing system to receive image signals from the data processing system; and a gain control device arranged to be operated by the user and to communicate gain adjustment signals to the data processing system. The data processing system is configured to provide the image signals to the visual display system for displaying an image that is movable in position with respect to the user during motion of the user's head. The data processing system is further configured to determine a movement of the image during the motion of the user's head based on the head-motion signals and the gain adjustment signals, and the gain adjustment signals are provided for use in making an assessment of vestibulo-ocular function.

A method for assessing vestibulo-ocular function according to an embodiment of the current invention includes providing an image to a user, moving the image along spatial positions with a spatio-temporal pattern of motion that is at least partially dependent on concurrent motion of a user's head, adjusting the spatio-temporal pattern of motion based on a motion gain control input from the user such that the image appears stationary to the user during the concurrent motion of the user's head, and assessing the vestibulo-ocular function based on the motion gain control input from the user.

A system for assessing vestibulo-ocular function according to an embodiment of the current invention includes a visual display system configured to display a left image to the left eye of a user and a right image to the right eye of the user, a data processing system configured to communicate with the visual display system to provide left image and right image signals for displaying the respective left and right images, and an alignment control device arranged to be operated by the user and to provide alignment adjustment signals to the data processing system. The left image has a first position and first orientation relative to the user and the right image has a second position and second orientation relative to the user, the data processing system is configured to change at least one of the first position, the first orientation, the second position or the second orientation based on the alignment adjustment signals, and the alignment adjustment signals are provided for use in assessing vestibulo-ocular function.

A method for assessing vestibulo-ocular function according to an embodiment of the current invention includes providing a left image to the left eye of a user, providing a right image to the right eye of the user, adjusting an alignment of the left image with the right image based on input from the user such the left and right images appear to be aligned to the user, and assessing the vestibulo-ocular function based on the adjusting by the user.

BRIEF DESCRIPTION OF THE DRAWINGS

Further objectives and advantages will become apparent from a consideration of the description, drawings, and examples.

DETAILED DESCRIPTION

Figure 1:
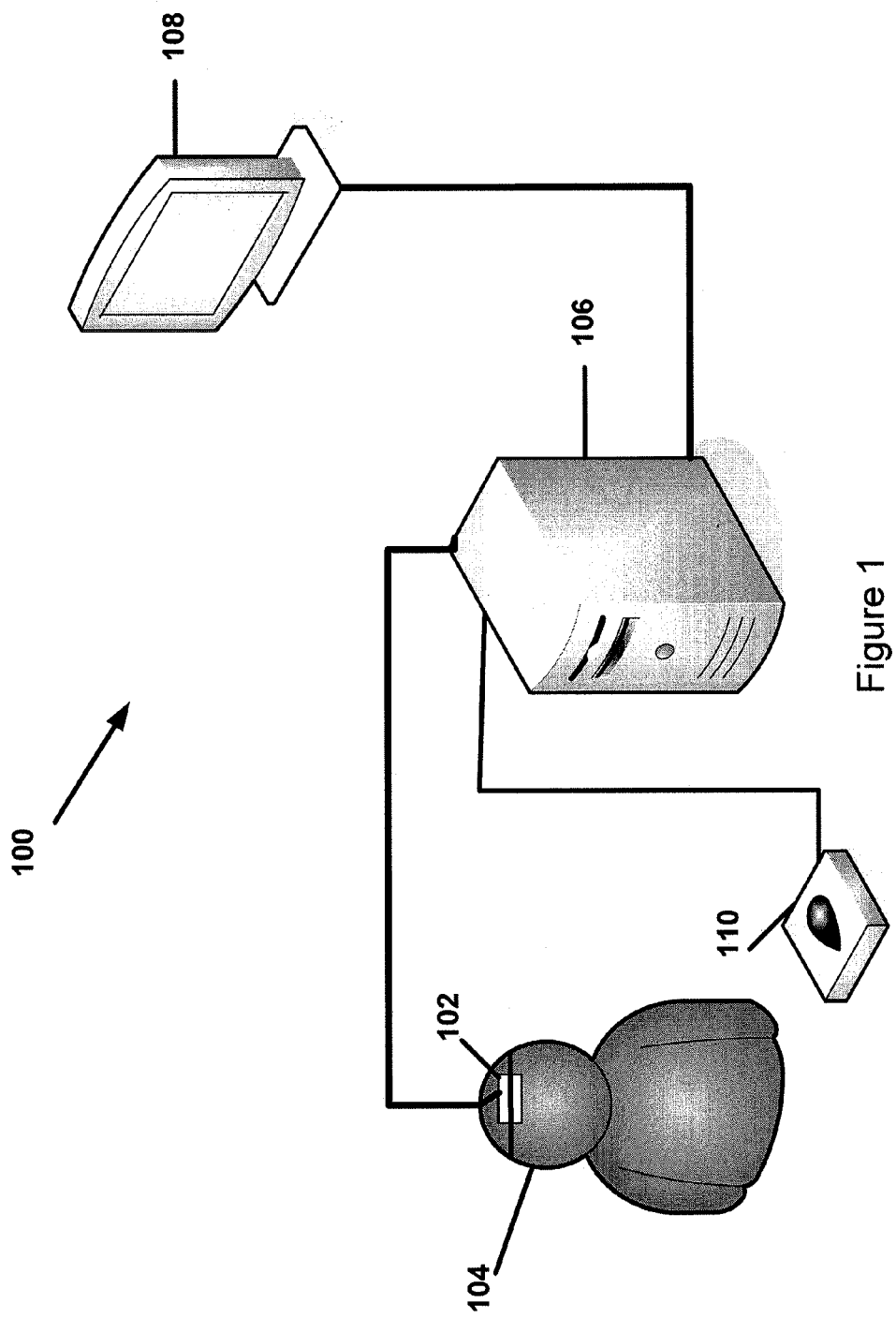
FIG. 1 provides a schematic illustration of a system for assessing vestibulo-ocular function according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

If a person's vestibulo-ocular reflex (VOR) is miscalibrated (i.e., the eye movements do not appropriately compensate for head movements), a stationary target will appear to move when the head moves (oscillopsia). If head movement is measured in real time, and used to control target motion through a variable gain, the subject can adjust that gain so that the target appears stationary during head motion. The motion-gain setting determines to what extent the target must be moved—either more or less than the head movement—so that it matches the eye movements and appears to be stationary. If the VOR gain is too low, the eyes move less than the head (in the opposite direction), and the motion-gain setting will be less than 1.0 in order to null the perceived target movement. Likewise a VOR gain that is too high will lead to a motion-gain setting greater than 1.0. Thus the motion-gain value, set by the subject to null perceived target movement, provides a surrogate measure of VOR gain, without measuring eye movements.

A system for assessing vestibulo-ocular function according to an embodiment of the current invention can allow one to assess vestibulo-ocular function without the need to measure eye movements directly. We also refer to the system for assessing vestibulo-ocular function according to some embodiments of the current invention as a vestibulo-ocular nulling device (VOND). As the head is moved, if the eyes do not move appropriately to stabilize eye position, a visual target will undergo illusory motion (oscillopsia), proportional to the amount by which eye motion is deficient in compensating for head motion. VOND measures head motion according to an embodiment of the current invention and uses it to control target position; the subject controls the gain of target motion (relative to head motion) in order to null the apparent motion of the target. This provides a surrogate measure of vestibulo-ocular function.

Since it does not distinguish between VOR slow phases and catch-up saccades. VOND is a measure of functional performance—it does not care about the relative contribution of each component to gaze stabilization. This is a useful measure in clinical rehabilitation, where alternative strategies for vestibular compensation are desired and promoted. Dynamic visual acuity, an accepted measure in clinical settings, is similar in this regard. VOND provides an approximate measure, rather than a highly precise VOR gain estimate. This is adequate in many situations, such as the clinical-rehab setting just mentioned, where a rough and rapid estimate of VOR function could prove useful at the start and end of each clinic visit. This can enable non-invasive and non-contact tracking of improvements in performance between and within visits, for example. Home use for the same purpose can also be implemented according to an embodiment of the current invention. In some lab experiments as well, it may be sufficient to have an approximate gain measure. An example is in adaptation experiments, where VOR gain is to be changed over multiple sessions on different days. In some embodiments of the current invention, the system for assessing vestibulo-ocular function can include additional tests other than the above-noted dynamic nulling, for example, for otolith assessment. Other potential uses include testing in the field, for example for rapid vestibular assessment in military units, or for assessment of astronauts immediately upon return to earth (or landing on other bodies) possibly in remote areas far from standard measurement facilities.

FIG. 1 is a schematic illustration of a system 100 for assessing vestibulo-ocular function according to an embodiment of the current invention. The system 100 includes a motion sensor system 102 adapted to be coupled to a user's head 104. The motion sensor system 102 provides head-motion signals based on motion of the user's head 104. The system 100 also includes a data processing system 106 configured to communicate with the motion sensor system 102 to receive the head-motion signals, a visual display system 108 configured to communicate with the data processing system 106 to receive image signals from the data processing system 106, and a gain control device 110 arranged to be operated by the user and to communicate gain adjustment signals to the data processing system 106. The data processing system 106 is configured to provide the image signals to the visual display system 108 for displaying an image that is movable in position with respect to the user during motion of the user's head 104. The data processing system 106 is further configured to determine a movement of the image during the motion of the user's head 104 based on the head-motion signals and the gain adjustment signals, and the gain adjustment signals are provided for use in making an assessment of vestibulo-ocular function.

The motion sensor system 102 can be adapted to be coupled to a user's head 104 in a wide variety of ways. For example, motion sensors can be worn by the user in a headband, a helmet, a hat, on eye glasses or a head-mounted display. In other embodiments, motion sensors can be attached to bite boards such that the users can bite down on the bite boards so that the sensors are coupled to the user's head. However, the concepts of the current invention are not limited to these particular examples. In some embodiments of the current invention, the motion sensor system can include an angular rate sensor. For example, the angular rate sensor can be a one-axis, two-axis or three-axis angular rate sensor, such as, but not limited to one, two or three-axis gyroscopes, respectively. Head an image motions are not limited to only horizontal directions. The can also in vertical directions, or generally any three orthogonal rotation directions, or combinations thereof.

In some embodiments, MEMS gyros can be used, but the broad concepts of the current invention are not limited to these examples.

The visual display system 108 can include an electronic panel display according to some embodiments of the current invention. For example, the electronic panel display can be, but is not limited to, at least one of an LCD, LED, OLED or plasma electronic panel display. In other embodiments, the visual display system 108 can include a head-mounted display. In other embodiments, the visual display system 108 can include a projection display system. Such projection display systems can include large screen TVs and/or video projectors, for example. Other examples of projectors can include a laser source that provides a spot or extended image on a wall or a screen after being reflected from one or more controllable mirrors, for example. However, the visual display system 108 is not limited to these particular examples.

The visual display provides a target or scene that will be readily interpreted by the user as existing "in space" rather than on the display itself. For example, this can be achieved with, but is not limited to, a small head-mounted virtual-reality display, the laptop screen, or a laser projected on a wall or screen. Alternatively, a high-performance head-mounted display or a large computer monitor can be suitable for ease of use and to provide an intuitive scene. Various types of images can also be used, such as, but not limited to, dot targets, lines, and/or full-field images.

The data processing system 106 can be at least a portion of one of a tablet, a lap top or a personal computer, for example. In some embodiments, the data processing system 106 can be part of and/or distributed over a network, such as, but not limited to, a local area network (LAN) and/or the interne, for example.

The motion sensor system 102, the gain control device 110 and the display system 108 can communicate with the data processing system 106 by wired or wireless connections. Wireless communication can be through the Bluetooth protocol, for example. However, the concepts of the current invention are not limited to these examples of providing a communications link between the motion sensor system 102 and the data processing system 106.

Figure 2:
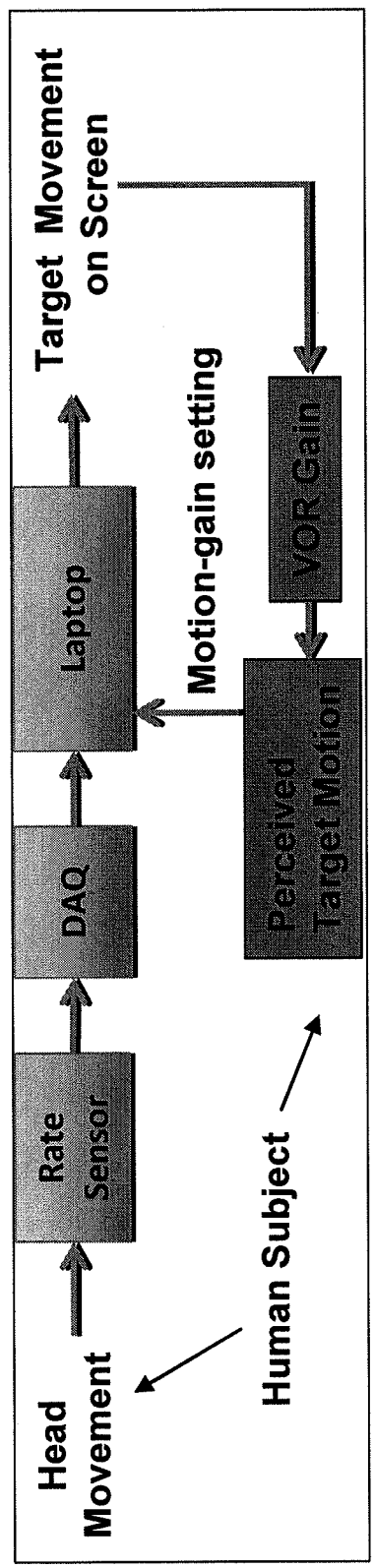
FIG. 2 is a flow chart illustrating some concepts of a system for assessing vestibulo-ocular function according to an embodiment of the current invention.

In operation, the system 100 for assessing vestibulo-ocular function according to an embodiment of the current invention utilizes perceptual reporting of oscillopsia by the user. As the user's head is moved, if the eyes do not move appropriately to stabilize eye position, a visual target will undergo illusory motion (oscillopsia), proportional to the amount by which eye motion is deficient in compensating for head motion. The system 100 measures head motion and uses it to control target position; the subject controls the gain of target motion (relative to head motion) in order to reduce the apparent motion of the target to zero. FIG. 2 provides a schematic illustration of this process. This provides a surrogate measure of vestibulo-ocular function. In the example of FIG. 2, a biteboard, 3D rate sensor (attached to the biteboard), data acquisition card, and laptop computer were used. In this example, head movements are measured by the 3D rate sensor and sent to the computer via the data acquisition card. The computer drives a visual display (head mounted, or the computer screen itself), which shows a visual target whose position on the screen is determined by the movement of the head and a motion-gain value set by the subject through a potentiometer.

If the vestibulo-ocular reflex (VOR) is miscalibrated (i.e., the eye movements do not appropriately compensate for head movements, as is the case with vestibular pathology), a stationary target will appear to move when the head moves (oscillopsia). If head movement is measured in real time, and used to control target motion through a variable gain, the subject can adjust that gain so that the target appears stationary during head motion. The motion-gain setting determines to what extent the target must be moved—either more or less than the head movement—so that it matches the eye movements and appears to be stationary. If the VOR gain is too low, the eyes move less than the head (in the opposite direction), and the motion-gain setting will be less than 1.0 in order to null the perceived target movement. Likewise a VOR gain that is too high will lead to a motion-gain setting greater than 1.0. Thus the motion-gain value, set by the subject to null perceived target movement, provides a surrogate measure of VOR gain, without measuring eye movements.

A method for assessing vestibulo-ocular function according to an embodiment of the current invention includes providing an image to a user, moving the image along spatial positions with a spatio-temporal pattern of motion that is at least partially dependent on concurrent motion of a user's head, adjusting the spatio-temporal pattern of motion based on a motion gain control input from the user such that the image appears stationary to the user during the concurrent motion of the user's head, and assessing the vestibulo-ocular function based on the motion gain control input from the user.

Figure 3:
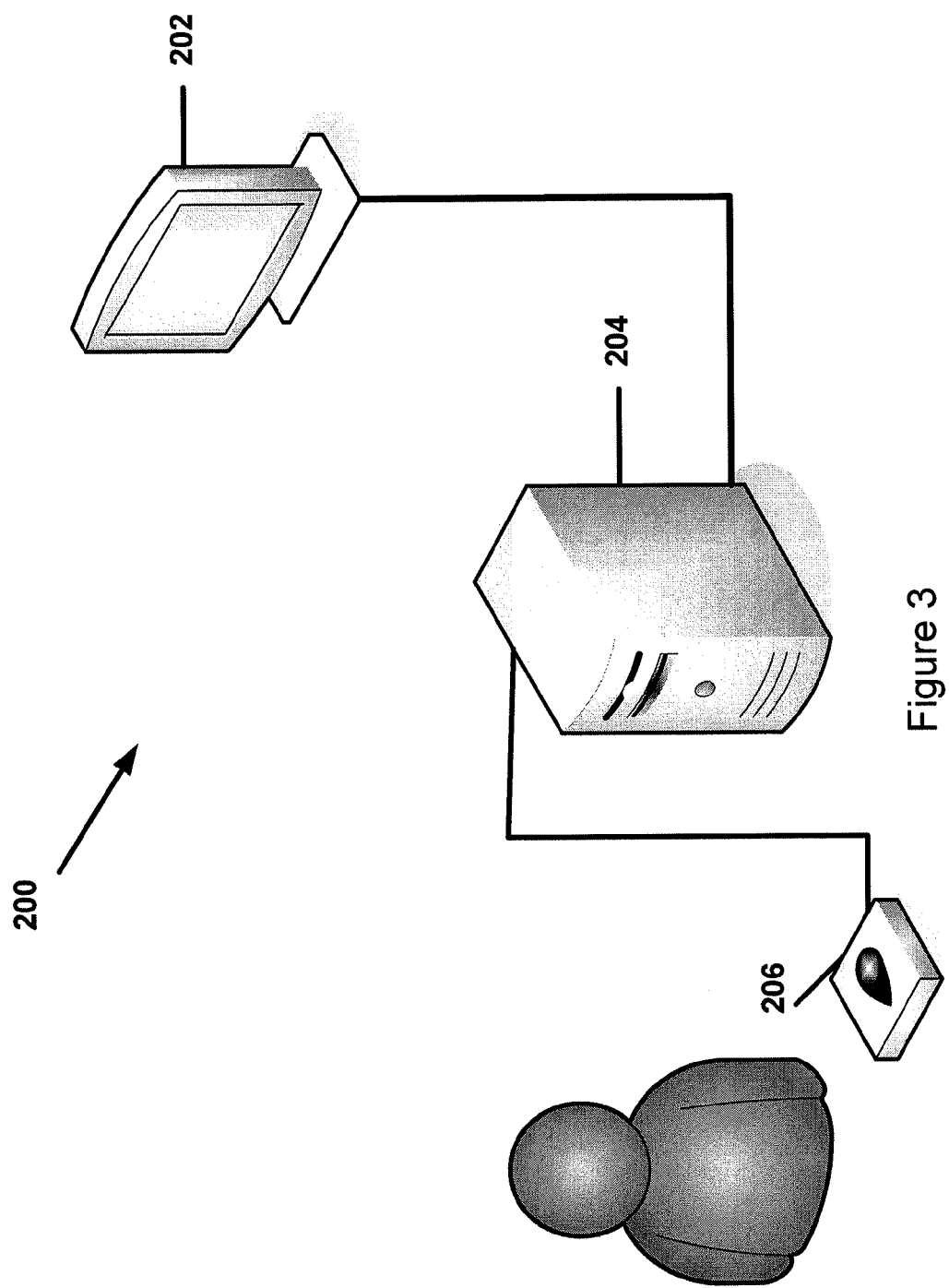
FIG. 3 provides a schematic illustration of a system for assessing vestibulo-ocular function according to another embodiment of the current invention.

FIG. 3 is a schematic illustration of a system 200 for assessing vestibulo-ocular function according to another embodiment of the current invention. The system 200 has a visual display system 202 that is configured to display a left image to the left eye of a user and a right image to the right eye of the user. This can be achieved, for example, by including glasses for the user that have a filter over each eye. The filters can be, but are not limited to color filters, polarizers and/or LCD shutters, for example. Alternatively, a head-mounted display can direct the left and right images to the respective left and right eyes, for example.

Figure 4:
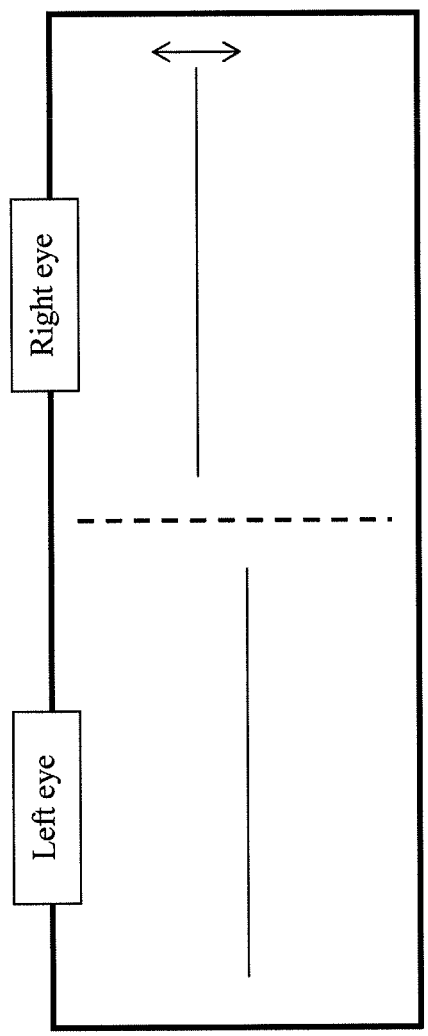
FIG. 4 shows an example of a visual display from a subject's point of view for assessing vertical skew using the system of FIG. 3.
Figure 5:
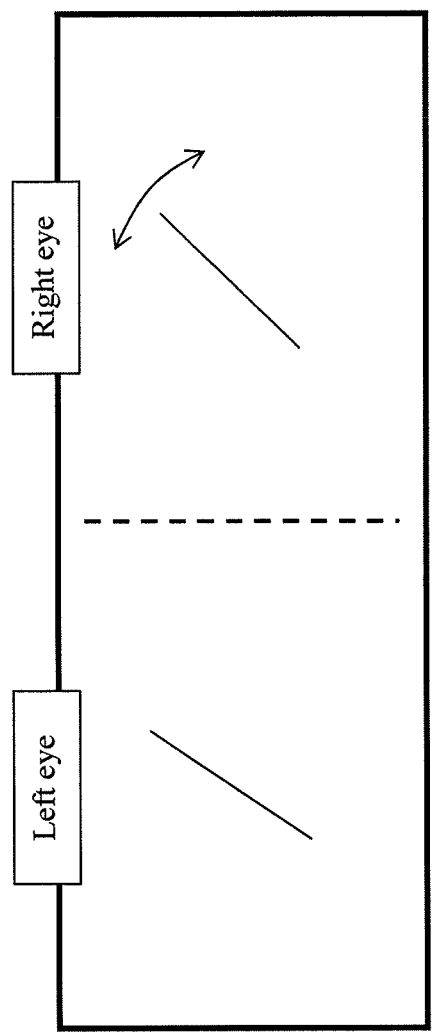
FIG. 5 shows an example of a visual display from a subject's point of view for assessing torsional disconjugacy using the system of FIG. 3.

The system 200 also includes a data processing system 204 that is configured to communicate with the visual display system 202 to provide left image and right image signals for displaying the respective left and right images. An alignment control device 206 is arranged to be operated by the user and to provide alignment adjustment signals to the data processing system 204. The left image has a first position and first orientation relative to the user and the right image has a second position and second orientation relative to the user. FIGS. 4 and 5 show two examples of left and right image pairs, as viewed by the user. The data processing system 204 is configured to change at least one of the first position, the first orientation, the second position or the second orientation based on the alignment adjustment signals, and the alignment adjustment signals are provided for use in assessing vestibulo-ocular function.

According to an embodiment of the current invention, the left image and the right image have an identifiable horizontal pattern relative to the user, and the data processing system is configured to change at least one of the first position or the second position based on the alignment adjustment signals to change a relative displacement in a vertical direction between the right and left images such that the right and left images appear to the user to be aligned. FIG. 4 provides one particular example in which the right and left images are each horizontal lines. In this example, the right image presented to the right eye of the user appears to the user to be higher in a vertical direction than the left image presented to the left eye. The arrow indicates that the image of the horizontal line presented to the right eye is movable up and down by the alignment control device 206. In other embodiments, the image to the left eye could alternatively, or additionally, can be movable by the alignment control device 206.

According to another embodiment of the current invention, the left image and the right image have an identifiable orientation pattern relative to the user, and the data processing system is configured to change at least one of the first orientation or the second orientation based on the alignment adjustment signals to change a relative orientation between the right and left images such that the right and left images appear to the user to be aligned. FIG. 5 provides one particular example in which the right and left images are each straight lines. In this example, the right image presented to the right eye of the user appears to the user to be rotated more in the clockwise direction than the left image presented to the left eye. The arrow indicates that the image of the line presented to the right eye can be rotated by the alignment control device 206. This is one example of adjusting the orientation, i.e., by rotation, to align the right and left images. In other embodiments, the image to the left eye could alternatively, or additionally, can be rotated by the alignment control device 206.

A method for assessing vestibulo-ocular function according to another embodiment of the current invention includes providing a left image to the left eye of a user, providing a right image to the right eye of the user, adjusting an alignment of the left image with the right image based on input from the user such the left and right images appear to be aligned to the user, and assessing the vestibulo-ocular function based on the adjusting by the user.

According to some embodiments, the system 100 can be combined together with system 200 to provide both dynamic and static assessments of vestibulo-ocular function in one system.

Other embodiments of the current invention can include, but are not limited to, the following dynamic testing:

1. With a fixed motion-gain setting, the subject can make head movements, observe the motion of the image on the display, and then use the knob/keyboard to set the length of a line so that this length matches the amount of perceived image motion when head movements were being made. This is a post hoc measure, in which the amount of oscillopsia is reported, rather than attempting to null that oscillopsia.
2. The knob/keyboard now sets a motion gain. Instead, this device can be used to control the motion of the visual image directly (i.e., turning the knob CW moves the image up, CCW moves it down). In this implementation, when head movements are made, the knob is constantly adjusted so that the image appears stationary. This provides an alternative way to do the nulling.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. A system for assessing vestibulo-ocular function, comprising:
    a motion sensor system adapted to be coupled to a user's head, wherein said motion sensor system provides head-motion signals based on motion of said user's head;
    a data processing system configured to communicate with said motion sensor system to receive said head-motion signals;
    a visual display system configured to communicate with said data processing system to receive image signals from said data processing system; and
    a gain control device arranged to be operated by said user and to communicate gain adjustment signals to said data processing system,
    wherein said data processing system is configured to provide said image signals to said visual display system for displaying an image that is movable along spatial positions with a spatio-temporal pattern of motion that is at least partially dependent on concurrent motion of said user's head,
    wherein said data processing system is further configured to determine a movement of said image during said motion of said user's head based on said head-motion signals and said gain adjustment signals,
    wherein said data processing system is further configured to adjust said spatio-temporal pattern of motion based on said gain adjustment signals from said user such that said image is moved during said concurrent motion of said user's head such that said image appears stationary to said user during said concurrent motion of said user's head, and
    wherein said user controlled gain adjustment signals are provided for use in making an assessment of vestibulo-ocular function.

2. A system for assessing vestibulo-ocular function according to claim 1, wherein said motion sensor system is an angular rate sensor system.

3. A system for assessing vestibulo-ocular function according to claim 2, wherein said angular rate sensor system comprises a gyroscope.

4. A system for assessing vestibulo-ocular function according to claim 2, wherein said angular rate sensor system comprises a three-axis gyroscope.

5. A system for assessing vestibulo-ocular function according to claim 1, wherein said visual display system comprises an electronic panel display.

6. A system for assessing vestibulo-ocular function according to claim 5, wherein said electronic panel display is at least one of an LCD, LED, OLED or plasma electronic panel display.

7. A system for assessing vestibulo-ocular function according to claim 1, wherein said visual display system comprises a head-mounted display.

8. A system for assessing vestibulo-ocular function according to claim 1, wherein said visual display system comprises a projection display system.

9. A system for assessing vestibulo-ocular function according to claim 1, wherein said data processing system is at least a portion of one of a tablet, a laptop, or a personal computer.

* * * * *